United States Patent [19]

Jeffries, III et al.

[11] Patent Number: 4,992,596
[45] Date of Patent: Feb. 12, 1991

[54] SELECTED TRINUCLEAR NOVOLAK OLIGOMERS AND THEIR USE IN PHOTOACTIVE COMPOUNDS AND RADIATION SENSITIVE MIXTURES

[75] Inventors: Alfred T. Jeffries, III, Providence, R.I.; Andrew J. Blakeney, Seekonk, Mass.; Medhat A. Toukhy, Barrington, R.I.

[73] Assignee: Olin Hunt Specialty Products Inc., Cheshire, Conn.

[21] Appl. No.: 534,908

[22] Filed: Jun. 8, 1990

Related U.S. Application Data

[62] Division of Ser. No. 290,009, Dec. 27, 1988, Pat. No. 4,957,846.

[51] Int. Cl.$^5$ .............................................. C07C 39/12
[52] U.S. Cl. .................... 568/720; 568/718; 430/165; 430/190; 430/192; 534/557
[58] Field of Search ................ 568/718, 720; 430/165, 430/190, 192; 534/557

[56] References Cited

U.S. PATENT DOCUMENTS

| | | | |
|---|---|---|---|
| 3,288,864 | 11/1961 | Farnham | 568/720 |
| 3,384,618 | 5/1968 | Imoto et al. | |
| 3,414,542 | 12/1968 | Vitrone | 568/720 |
| 4,407,926 | 10/1983 | Stahlhofen | 430/193 |
| 4,439,511 | 3/1984 | Stahlhofen | 430/193 |
| 4,477,553 | 10/1984 | Yamamoto et al. | 430/192 |
| 4,587,196 | 5/1986 | Toukhy | 430/192 |
| 4,614,826 | 9/1986 | Katayama et al. | 549/559 |
| 4,642,282 | 2/1987 | Stahlhofen | 430/192 |
| 4,837,121 | 6/1989 | Blakeney et al. | 430/192 |

FOREIGN PATENT DOCUMENTS

| | | | |
|---|---|---|---|
| 117759 | 5/1984 | European Pat. Off. | 430/190 |
| 0225034 | 12/1983 | Japan | 568/720 |
| 62-10646A | 1/1987 | Japan | 430/190 |

*Primary Examiner*—Werren B. Lone
*Attorney, Agent, or Firm*—William A. Simons

[57] ABSTRACT

A trinuclear novolak oligomer of the formula (I):

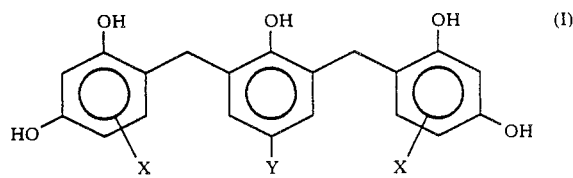

wherein each X is selected from the group consisting of hydroxyl group and halide group and Y is selected from the group consisting of a lower alkyl group having 1–4 carbon atoms and halogen atom.

5 Claims, No Drawings

SELECTED TRINUCLEAR NOVOLAK OLIGOMERS AND THEIR USE IN PHOTOACTIVE COMPOUNDS AND RADIATION SENSITIVE MIXTURES

This application is a division of application Ser. No. 07/290,009, filed Dec. 27, 1988.

BACKGROUND OF THE INVENTION

1. Field of the Invention

The present invention relates to selected trinuclear novolak oligomers useful as backbones for certain photoactive compounds. Further, the present invention relates to such photoactive compounds formed by the esterification of these trinuclear novolak oligomers with sulfonyl halides of o-naphthoquinone diazides. Still further, the present invention also relates to radiation sensitive mixtures (e.g. those particularly useful as positive-working photoresists) containing the combination of these photoactive compounds with alkali-soluble binder resins dissolved in a solvent. And furthermore, the present invention also relates to substrates coated with these radiation sensitive mixtures as well as the process of coating, imaging and developing these radiation sensitive mixtures on these substrates.

2. Description of Related Art

Photoresist compositions are used in microlithographic processes for making miniaturized electronic components such as in the fabrication of integrated circuits and printed wiring board circuitry. In these processes, a thin coating or film of a photoresist composition is generally first applied to a substrate material, such as silicon wafers used for making integrated circuits or aluminum or copper plates of printed wiring boards. The coated substrate is then baked to evaporate any solvent in the photoresist composition and to fix the coating onto the substrate. The baked coated surface of the substrate is next subjected to an image-wise exposure of radiation. This radiation exposure causes a chemical transformation in the exposed areas of the coated surface. Visible light, ultraviolet (UV) light, electron beam, ion beam and X-ray radiant energy are radiation types commonly used today in microlithographic processes.

After this image-wise exposure, the coated substrate is treated with a developer solution to dissolve and remove either the radiation-exposed or the unexposed areas of the coated surface of the substrate. In some processes, it is desirable to bake the imaged resist coating before this developing step. This intermediate step is sometimes called post-exposure bake or PEB.

There are two types of photoresist compositions—negative-working and positive-working. When negative-working photoresist compositions are exposed image-wise to radiation, the areas of the resist composition exposed to the radiation become less soluble to a developer solution (e.g. a cross-linking reaction occurs) while the unexposed areas of the photoresist coating remain relatively soluble to a developing solution. Thus, treatment of an exposed negative-working resist with a developer solution causes removal of the non-exposed areas of the resist coating and the creation of a negative image in the photoresist coating, and thereby uncovering a desired portion of the underlying substrate surface on which the photoresist composition was deposited. On the other hand, when positive-working photoresist compositions are exposed image-wise to radiation, those areas of the resist composition exposed to the radiation become more soluble to the developer solution (e.g. the Wolff rearrangement reaction of the photoactive compound occurs) while those areas not exposed remain relatively insoluble to the developer solution. Thus, treatment of an exposed positive-working resist with the developer solution causes removal of the exposed areas of the resist coating and the creation of a positive image in the photoresist coating. Again, a desired portion of the underlying substrate surface is uncovered.

Positive-working photoresist compositions are currently favored over negative-working resists because the former generally have better resolution capabilities and pattern transfer characteristics.

After this development operation, the now partially unprotected substrate may be treated with a substrate-etchant solution or plasma gases and the like. This etchant solution or plasma gases etch the portion of the substrate where the photoresist coating was removed during development. The areas of the substrate are protected where the photoresist coating still remains and, thus, an etched pattern is created in the substrate material which corresponds to the photomask used for the image-wise exposure of the radiation. Later, the remaining areas of the photoresist coating may be removed during a stripping operation, leaving a clean etched substrate surface. In some instances, it is desirable to heat treat the remaining resist layer after the development step and before the etching step to increase its adhesion to the underlying substrate and its resistance to etching solutions.

End users of photoresists are demanding photoresist formulations which possess better lithographic properties for the fabrication of smaller microelectronic circuits. The lithographic properties which are critical to these end-users include the following: (1) good resolution capabilities in both the micron and submicron ranges without incomplete development in the exposed areas (i.e. scumming); (2) higher thermal image deformation temperatures (e.g. above 120° C.); (3) relatively fast photospeeds; (4) good adhesion to substrate; (5) good developer dissolution rates; (6) good process latitute; (7) near to absolute vertical profiles (or good contrast) between exposed and unexposed photoresist areas after development; (8) good resistance to etching solutions and plasma etching techniques; (9) reduced tendency to form insoluble particulates and (10) mask linearity.

Generally, in the past efforts to improve one of these lithographic properties have caused significant decreases in one or more of the other lithographic properties of the photoresist. Accordingly, there is a need for improved photoresist formulations which possess all of these desired properties. The present invention is believed to be an answer to that need.

In the past, reactions between 2,6-bis(hydroxymethyl)-p-cresol and alkyl monohydric phenols to form novolak oligomers have been known. These novolak oligomers were then reacted with 6-diazo-5,6-dihydro-5-oxo-1-naphthalene-1-sulfonic acid to form a photoactive compound and then used to make a positive-working photoresist. See Japanese Patent Publication (Kokai) No. 62-10646(A) assigned to Kanto Chemical Company and published on Jan. 19, 1987. One of the novolak oligomers taught by this reference has the following formula (PA-I):

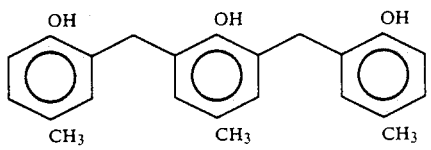

Separately, reaction between 2,6-bis(hydroxymethyl)-p-cresol and resorcinol to form oligomeric polyhydric phenol novolaks were then reacted with epihalohydrin or the like to form a polyglycidic ether which was combined with curing agent to form a curable epoxy resin composition. See U.S. Pat. No. 4,614,826, which issued to Katayama et al on Sept. 30, 1986. The reaction product of 2,6-bis(hydroxymethyl)-p-cresol and resorcinol according to this reference has the following chemical formula (PA II):

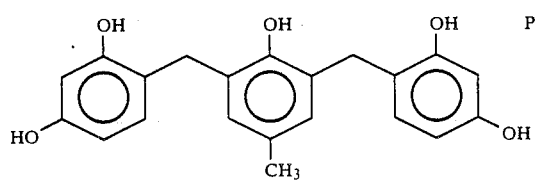

SUMMARY OF THE INVENTION

Accordingly, the present invention is directed to selected trinuclear novolak oligomers of formula (I):

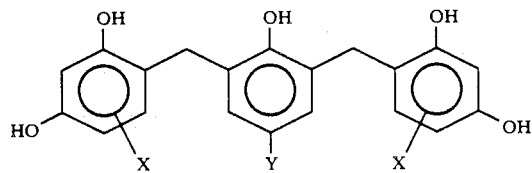

wherein each X is selected from the group consisting of hydroxyl group and halogen group (i.e. Cl, Br, I and F); and Y is selected from the group consisting of a lower alkyl group having from 1 to 4 carbon atoms and halogen atom.

Moreover, the present invention is directed to photoactive o-naphthoquinone diazide sulfonyl moieties of said novolak oligomer compounds having formula (II):

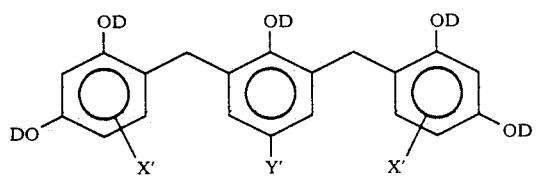

wherein each X' is selected from the group consisting of hydrogen, OD and halogen; wherein Y' is selected from the group consisting of a lower alkyl having 1 to 4 carbon atoms and halogen atom; and wherein each D is a o-naphthoquinone diazide sulfonyl moiety or a hydrogen atom, with the proviso at least two D's are o-naphthoquinone diazide sulfonyl moieties.

Moreover, the present invention is directed to a radiation sensitive mixture useful as a positive photoresist comprising an admixture of at least one photoactive o-naphthoquinone diazide compound of formula (II) above and an alkali-soluble binder resin; the amount of said photoactive o-naphthoquinone diazide compound or compounds being about 5% to about 40% by weight and the amount of said binder resin being about 60% to 95% by weight, based on the total solids content of said radiation sensitive mixture.

Still further, the present invention also encompasses the process of coating substrates with these radiation sensitive mixtures and then exposing and developing these coated substrates.

Also further, the present invention encompasses said coated substrates (both before and after imaging) as novel articles of manufacture.

DETAILED DESCRIPTION

The selected trinuclear novolak oligomers of formula I are made by reacting the corresponding -para-(lower alkyl or halo)-2,6-bis(hydroxymethyl) phenol (preferably 2,6-bis-(hydroxymethyl)-p-cresol) with a polyhydroxy phenyl compound (preferably, resorcinol, 4-chlororesorcinol, pyrogallol and phloroglucinol). This reaction is illustrated below in reaction equation (A) wherein X and Y are defined as above:

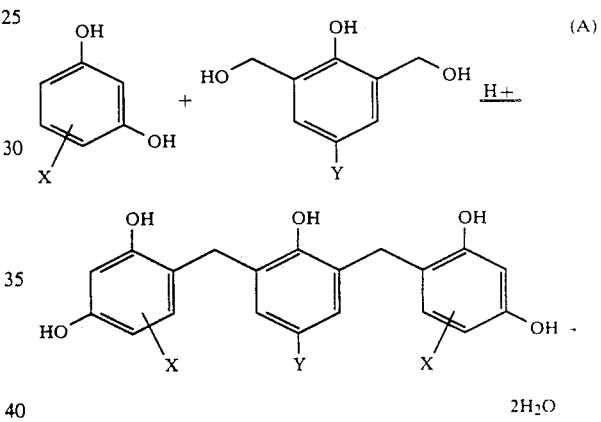

In making this class of novolak oligomers of the present invention, the precursors are preferably present in the reaction vessel in a mole ratio of polyhydroxy phenyl compound or compounds to the 2,6-bis(hydroxymethyl)phenol compound or compounds from about 5:1 to about 20:1, preferably from about 10:1 to about 15:1. The preferred reaction temperature is about 60°–100° C. for about 2 to 6 hours at atmospheric pressure. Preferably, this reaction occurs in the presence of a solvent and an acid catalyst. The preferred solvent is water. Suitable acid catalysts include those commonly employed in acid condensation-type reaction such as HCl, $H_3PO_4$, $H_2SO_4$, oxalic acid, maleic acid, maleic anhydride and organic sulfonic acids (e.g. p-toluene sulfonic acid). The most preferred acid catalyst is p-toluene sulfonic acid. Excess reaction time may cause undesirable polymerization of the intended product. The preferred ratio of total solids to water is preferably about 0.1 grams to about 0.5 grams total solids per milliliter of solvent.

This condensation reaction will form a mixture of oligomeric novolak species of different molecular weight. When a large molar excess of the polyhydroxy phenyl compound precursor is employed, the major portion by weight of product mixture is the trinuclear novolak oligomer of formula (I). The present invention encompasses both substantially pure trinuclear novolak oligomers of formula (I) as well as mixtures of such trinuclear novolaks with other species formed by this condensation reaction.

The intended product may be recovered from the reaction mixture by first cooling to room temperature or less, then diluting the reaction mixture with more solvent (i.e. water) and then isolating the solid product by filtration. This crude product may be washed with water and directly dried or, alternatively, after isolation it may be redissolved in acetone and filtered before solvent evaporation.

The preferred novolak oligomers are made from the reaction of 2,6-bis(hydroxymethyl)-p-cresol with resorcinol (see formula IA); with 4-chlororesorcinol (see formula IB); with pyrogallol (see formula IC); and with phloroglucinol (see formula ID), all of which are as follows:

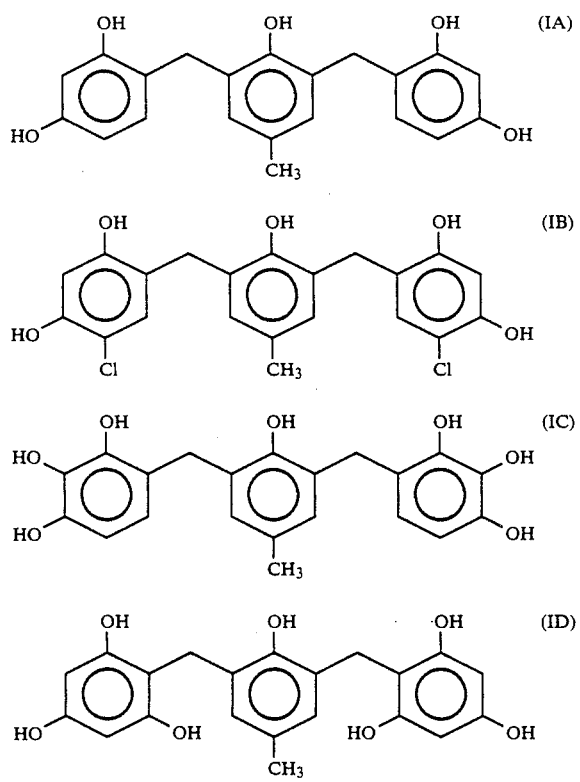

The novolak oligomers of this invention may be converted into the photoactive compounds (PACs) of formula II by their condensation with o-naphthoquinone diazide sulfonyl compounds. Any o-naphthoquinone diazide sulfonyl compound used in making photoresist sensitizers may be employed herein. The most preferred o-naphthoquinone diazide sulfonyl ester moieties are derived from 3-diazo-3,4-dihydro-4-oxo-naphthalene-1-sulfonic acid chloride (also known as 1,2-naphtho-quinone-(2)-diazo-4-sulfonic acid chloride or Diazo M) or 6-diazo-5,6-dihydro-5-oxo-naphthalene-1-sulfonic acid chloride (also known as 1,2-napthoquinone-(2)-diazo-5-sulfonic acid chloride or Diazo L). These 4- and 5-ester groups or moieties respectively have the following chemical formulae (III) and (IV):

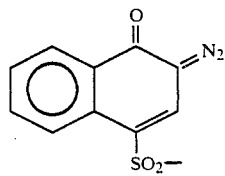

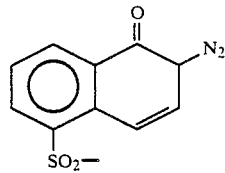

It is understood that present invention covers the use of o-naphthoquinone diazide sulfonyl moieties singly or in mixtures in the condensation reaction with these novolak oligomers. Also, the present invention encompasses separate reactions of these novolak oligomers with different o-naphthoquinone diazide sulfonyl moieties followed by blending those reaction products together.

This condensation reaction may be carried under any conventional ester condensation conditions. Preferably, these ester compounds of formula (II), above, are prepared by first dissolving the sulfonic acid halide precursor, preferably, the sulfonic acid chloride, in a suitable solvent. Suitable solvents include acetone, dioxane, gamma-butyrolactone, methylene chloride, tetrahydrofurfural alcohol and the like. The trinuclear novolak oligomer of formula (I) is then added to this solution. It is advantageous to carry out this reaction in the presence of an acid-scavenging base, such as alkali metal carbonates or bicarbonates, alkaline earth metal carbonates or bicarbonates, tertiary aliphatic amines or pyridine or pyridine derivatives.

The esterification products of this reaction may be recovered from the reaction mixture by any conventional means, preferably by precipitation into acidified water, followed by filtration and drying.

The preferred photoactive compounds (sometimes known as "sensitizers") are those made from the preferred novolak oligomer precursors listed above, namely, 2,6-bis(hydroxymethyl)-p-cresol with resorcinol (see formula IIA); with 4-chlororesorcinol (see formula IIB); with pyrogallol (see formula IIC); and with phloroglucinol (see formula IID), all of which are as follows:

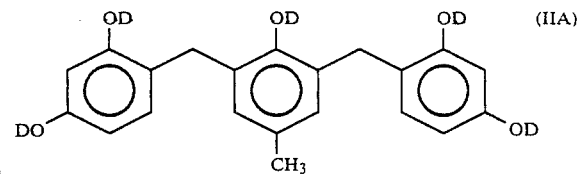

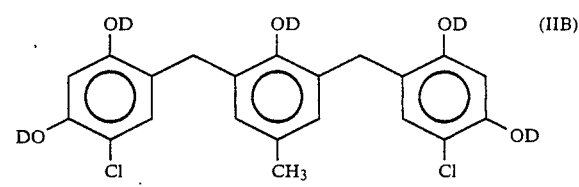

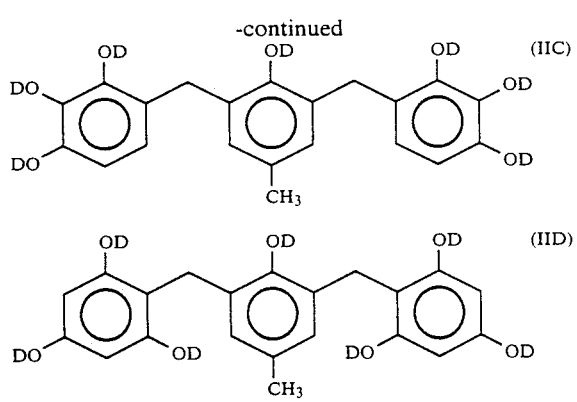

In these photoactive compounds, the D is most preferably 3-diazo-3,4-dihydro-4-oxo-naphthalene-1-sulfonyl; 6-diazo-5,6-dihydro-5-oxo-naphthalene-1-sulfonyl or hydrogen with the proviso that at least three of the Ds are one or both of said sulfonyl moieties.

At least one of the ester compounds of the present invention may be mixed with an alkali-soluble resin or resins to make radiation sensitive mixtures which are useful as positive-working photoresist compositions. The term "alkali-soluble resin" is used herein to means a resin which will dissolve completely in an aqueous alkaline developing solution conventionally used with positive-working photoresist compositions. Suitable alkali-soluble resins include phenol-formaldehyde novolak resins, cresol-formaldehyde novolak resins, and polyvinyl phenol resins, preferably having a molecular weight of about 500 to about 40,000, and more preferably from about 800 to 20,000. These novolak resins are preferably prepared by the condensation reaction of phenol or cresols with formaldehyde and are characterized by being light-stable, water-insoluble, alkali-soluble and film-forming. The most preferred class of novolak resins is formed by the condensation reaction between a mixture of meta- and para-cresols with formaldehyde having a molecular weight of about 1,000 to about 10,000. The preparation of examples of such suitable resins is disclosed in U.S. Pat. Nos. 4,377,631; 4,529,682; and 4,587,196, all which issued to Medhat Toukhy and are incorporated herein by references in their entireties.

Other photoactive compounds may also be added to the radiation sensitive mixtures of the present invention. These other photoactive compounds may include o-quinonediazide esters derived from polyhydric phenols, alkyl-polyhydroxyphenones, aryl-polyhydroxyphenones, and the like which can contain up to six or more sites for esterification. The most preferred o-quinonediazide esters are derived from 3-diazo-3,4-dihydro-4-oxo-naphthalene-1-sulfonic acid chloride and 6-diazo-5,6-dihydro-5-oxo-naphthalene-1-sulfonic acid chloride. When other photoactive compounds are used in radiation sensitive mixtures besides the photoactive compounds of the present invention, the amount of photoactive compounds of the present invention should be at least about 5% by weight, preferably 10-100% by weight of the total photoactive compounds present.

The proportion of the photoactive compound in the radiation sensitive mixture may preferably range from about 5 to about 40%, more preferably from about 10 to about 25% by weight of the non-volatile (e.g. non-solvent) content of the radiation sensitive mixture. The proportion of total binder resin of this present invention in the radiation sensitive mixture may preferably range from about 60 to about 95%, more preferably, from about 75 to 90% of the non-volatile (e.g. excluding solvents) solids content of the radiation sensitive mixture.

These radiation sensitive mixtures may also contain conventional photoresist composition ingredients such as solvents, actinic and contrast dyes, anti-striation agents, plasticizers, speed enhancers, and the like. These additional ingredients may be added to the binder resin and photoactive compound before the solution is coated onto the substrate.

The resins and sensitizers may be dissolved in a solvent or solvents to facilitate their application to the substrate. Examples of suitable solvents include methoxyacetoxy propane, ethyl cellosole acetate, n-butyl acetate, ethyl lactate, ethyl 3-ethoxy propionate, propylene glycol alkyl ether acetates, or mixtures thereof and the like. Cosolvents such as xylene or n-butylacetate may also be used. The preferred amount of solvent may be from about 50% to about 500%, or higher, by weight, more preferably, from about 100% to about 400% by weight, based on combined resin and sensitizer weight.

Actinic dyes help provide increased resolution on highly reflective surfaces by inhibiting back scattering of light off the substrate. This back scattering causes the undesirable effect of optical notching, especially on a highly reflective substrate topography. Examples of actinic dyes include those that absorb light energy at approximately 400-460 nm [e.g. Fat Brown B (C.I. No. 12010); Fat Brown RR (C.I. No. 11285); 2-hydroxy-1,4-naphthoquinone (C.I. No. 75480) and Quinoline Yellow A (C.I. No. 47000)]and those that absorb light energy at approximately 300-340 nm [e.g. 2,5-diphenyloxazole (PPO-Chem. Abs. Reg. No. 92-71-7) and 2-(4-biphenyl)-6-phenyl-benzoxazole (PBBO-Chem. Abs. Reg. No. 17064-47-0)]. The amount of actinic dyes may be up to ten percent weight levels, based on the combined weight of resin and sensitizer.

Contrast dyes enhance the visibility of the developed images and facilitate pattern alignment during manufacturing. Examples of contrast dye additives that may be used together with the radiation sensitive mixtures of the present invention include Solvent Red 24 (C.I. No. 26105), Basic Fuchsin (C.I. 42514), Oil Blue N (C.I. No. 61555) and Calco Red A (C.I. No. 26125) up to ten percent weight levels, based on the combined weight of resin and sensitizer.

Anti-striation agents level out the photoresist coating or film to a uniform thickness. Anti-striation agents may be used up to five percent weight levels, based on the combined weight of resin and sensitizer. One suitable class of anti-striation agents is non-ionic silicon-modified polymers. Non-ionic surfactants may also be used for this purpose, including, for example, nonylphenoxy poly(ethyleneoxy) ethanol; octylphenoxy (ethyleneoxy) ethanol; and dinonyl phenoxy poly(ethyleneoxy) ethanol.

Plasticizers improve the coating and adhesion properties of the photoresist composition and better allow for the application of a thin coating or film of photoresist which is smooth and of uniform thickness onto the substrate. Plasticizers which may be used include, for example, phosphoric acid tri-(B-chloroethyl)-ester; stearic acid; dicamphor; polypropylene; acetal resins; phenoxy resins; and alkyl resins up to ten percent weight levels, based on the combined weight of resin and sensitizer.

Speed enhancers tend to increase the solubility of the photoresist coating in both the exposed and unexposed areas, and thus, they are used in applications where speed of development is the overriding consideration even though some degree of contrast may be sacrificed, i.e. in positive resists while the exposed areas of the photoresist coating will be dissolved more quickly by the developer, the speed enhancers will also cause a larger loss of photoresist coating from the unexposed areas. Speed enhancers that may be used include, for example, picric acid, nicotinic acid or nitrocinnamic acid at weight levels of up to 20 percent, based on the combined weight of resin and sensitizer.

The prepared radiation sensitive resist mixture, can be applied to a substrate by any conventional method used in the photoresist art, including dipping, spraying, whirling and spin coating. When spin coating, for example, the resist mixture can be adjusted as to the percentage of solids content in order to provide a coating of the desired thickness given the type of spinning equipment and spin speed utilized and the amount of time allowed for the spinning process. Suitable substrates include silicon, aluminum or polymeric resins, silicon dioxide, doped silicon dioxide, silicon resins, gallium arsenide, silicon nitride, tantalum, copper, polysilicon, ceramics and aluminum/copper mixtures. The coating surfaces of these substrates may or may not be primed with a conventional adhesion promoter (e.g. hexamethyldisilazane) before the photoresist coating is applied.

The photoresist coatings produced by the above described procedure are particularly suitable for application to silicon wafers coated with a silicon dioxide or silicon nitride layer such as are utilized in the production of microprocessors and other miniaturized integrated circuit components. An aluminum or aluminum-coated substrates may be used as well. The substrate may also comprise various polymeric resins especially transparent polymers such as polyesters and polyolefins.

After the resist solution is coated onto the substrate, the coated substrate is baked at approximately 70° C. to 125° C. until substantially all the solvent has evaporated and only a uniform radiation sensitive coating remains on the substrate.

The coated substrate can then be exposed to radiation, especially ultraviolet radiation, in any desired exposure pattern, produced by use of suitable masks, negatives, stencils, templates, and the like. Conventional imaging process or apparatus currently used in processing photoresist-coated substrates may be employed with the present invention. While ultraviolet (UV) light is the preferred source of radiation, other sources of radiation such as visible light, electron or ion beam and x-ray radiant energy may be instead used.

The exposed resist-coated substrates are preferably subjected to a post exposure bake at a temperature from about 90° C. to about 120° C. from about 30–300 seconds to enhance image quality and resolution.

The exposed resist-coated substrates are next developed in an aqueous alkaline developing solution. This solution is preferably agitated, for example, by nitrogen gas agitation. Examples of aqueous alkaline developers include aqueous solutions of tetramethylammonium hydroxide, sodium hydroxide, potassium hydroxide, ethanolamine, choline, sodium phosphates, sodium carbonate, sodium metasilicate, and the like. The preferred developers for this invention are aqueous solutions of either alkali metal hydroxides, phosphates or silicates, or mixtures thereof, or tetramethylammonium hydroxide.

Alternative development techniques such as spray development or puddle development, or combinations thereof, may also be used.

The substrates are allowed to remain in the developer until all of the resist coating has dissolved from the exposed areas. Normally, development times from about 10 seconds to about 3 minutes are employed.

After selective dissolution of the coated wafers in the developing solution, they are preferably subjected to a deionized water rinse to fully remove the developer or any remaining undesired portions of the coating and to stop further development. This rinsing operation (which is part of the development process) may be followed by blow drying with filtered air to remove excess water. A post-development heat treatment or bake may then be employed to increase the coating's adhesion and chemical resistance to etching solutions and other substances. The post-development heat treatment can comprise the baking of the coating and substrate below the coating's thermal deformation temperature.

In industrial applications, particularly in the manufacture of microcircuitry units on silicon/silicon dioxide-type substrates, the developed substrates may then be treated with a buffered hydrofluoric acid etching solution or plasma gas etch. The resist compositions of the present invention are believed to be resistant to a wide variety of acid etching solutions or plasma gases and provide effective protection for the resist-coated areas of the substrate.

Later, the remaining areas of the photoresist coating may be removed from the etched substrate surface by conventional photoresist stripping operations.

The present invention is further described in detail by means of the following Examples. All parts and percentages are by weight unless explicitly stated otherwise.

EXAMPLE 1

Novolak Oligomer A 2,6-bis[(5-chloro-2,4-dihydroxyphenyl) methyl]-4-methylphenol A one liter three-necked reaction flask was fitted with a mechanical stirring apparatus, a Y arm, and a thermometer. To the flask was added 2,6-bis(hydroxymethyl)-p-cresol (recrystallized once from ethanol) (25.25 g, 0.15 mole), 4-chlororesorcinol (216.8 g, 1.50 mole), p-toluene sulfonic acid monohydrate (1.0 g), and water (300 mL). The reaction mixture was stirred and heated and to about 80 degrees C. and maintained at about 80 degrees C. for four hours.

The reaction mixture was cooled to room temperature and diluted with water (300 mL). The precipitated product was isolated by filtration and washed with water (3 L).

The solid product was air-dried at room temperature, dissolved in acetone (150 mL), filtered, and precipitated into water (2 L).

The precipitate was isolated and air-dried at 50 degrees C. to leave 50 g solid, 78% of theory.

The titled compound's purity and structure were established by its liquid chromatogram and its proton NMR and carbon NMR spectra.

The liquid chromatogram was obtained using a 5 micron 4.5 mm×250 mm $C_8$ end capped column. The mobile phase used is 45% HISB (high ionic strength buffer) 55% acetonitrile. The high ionic strength buffer is made from trifluoroacetic acid anhydride (1.5 mL), tetramethylammonium hydroxide pentahydrate (1.8 g) and water (1 L). The pH of this solution is adjusted to 3.0+/−0.1 with sodium hydroxide (0.1N). The flow is 2.5 mL/min. The chromatogram exhibited the following major peaks reported as retention time in minutes and (area percent); 2.1 min. (4.5%), 2.6 min. (67.9%), 4.4 min. (4.5%), 6.3 min. (6.1%).

The proton NMR of this oligomer was recorded in acetone $d_6$ with tetramethylsilane (TMS) as the internal standard. The chemical shifts of the major signals (all singlets) are reported as parts per million (ppm) downfield from TMS; 2.15 ppm, 3.82 ppm, 6.59 ppm, 6.87 ppm, 7.09 ppm.

The carbon-13 NMR spectrum of the above solid was recorded in dimethylsulfoxide-$d_6$ with tetramethylsilane (TMS) as the internal standard. The chemical shifts of the major signals are reported in parts per million (ppm) downfield from the TMS; 20.30 ppm, 28.79 ppm, 103.43 ppm, 109.23 ppm, 119.32 ppm, 127.50 ppm, 127.64 ppm, 128.32 ppm, 130.12 ppm, 149.86 ppm, 151.40 ppm, 154.01 ppm.

EXAMPLE 2

Novolak Oligomer B 2,6-Bis[(2,4-dihydroxyphenyl)methyl]-4-methylphenol

A one liter three-neck flask was fitted a mechanical stirring apparatus, a Y-arm and thermometer. To the flask was added 2,6-bis(hydroxymethyl)-p-cresol (recrystallized once from ethanol) (8.41 g 0.05 mole), resorcinol (82.6 g, 0.75 mole), p-toluene sulfonic acid monohydrate (1.37 g) and water (230 mL). The stirring was begun and the contents of the flask were heated for four hours at 72-95 degrees C.

After cooling in an ice bath, the resulting solid was isolated by filtration, washed with water (1.5L) and dried at 40-50 degrees C. under vacuum in a nitrogen atmosphere. The product weighed 13.3 g, 75% of theory.

The titled substance's purity and identity were established from its liquid chromatogram, proton NMR and carbon-13 NMR spectra.

The liquid chromatogram was obtained using a 10 cm Apex C 18 column. The mobile phase used is 55% HISB and 45% acetnitrile at a 1 mL/min. The chromatogram exhibited the following major peaks reported as retention time in minutes, and (area percent); 2.64 min. (83.0%), 7.44 min. (15.29%).

The proton NMR of the substance was recorded in methanol-$d_4$ with tetramethylsilane (TMS) as the internal standard. The chemical shifts of the major signals are reported as parts per million (ppm) downfield from TMS; 2.1 ppm, 3.75 ppm, 4.9 ppm, 6.26 ppm (doublet of doublets), 6.33 ppm (doublet), 6.74 ppm, 6.87 ppm (doublet).

A carbon-13 spectrum of the substance was recorded in mehanol-$d_4$ with tetramethylsilane (TMS) as the internal standard. The chemical shifts of the major signals are reported in ppm downfield from TMS; 20.71 ppm, 30.71 ppm, 103.37 ppm, 108.13 ppm, 119.99 ppm, 129.36 ppm, 129.68 ppm, 130.23 ppm, 131.97 ppm, 150.18 ppm, 155.82 ppm, 157.52 ppm.

EXAMPLE 3

Novolak Oligomer C 2,6-Bis-[(2,3,4-trihydroxyphenyl)methyl]-4-methylphenol

A one Liter three neck flask was fitted with a mechanical stirring apparatus, a Y-arm and a thermometer. To the flask was added 2,6-bis(hydroxymethyl)-p-cresol(recrystallized once from ethanol) (18.29 g, 0.1087 mole), pyrogallol (206 g, 1.63 mole), p-toluenesulfonic acid monohydrate (3.36 g), and water (800 mL). The stirring was begun and the mixture was heated to about 65 degrees C. and maintained at this temperature for four hours.

After cooling in an ice bath, the resulting solid was isolated by filtration and dried under reduced pressure to leave 23 g solid, 55% of theory. The solid was dissolved in boiling water (200 mL), filtered, the solution concentrated to about 150 mL and allowed to recrystallize at room temperature. The solid was isolated by filtration and dried to leave 18.2 g.

The titled compound's purity and identity was established by its liquid chromatogram, proton NMR and carbon-13 NMR spectra.

The liquid chromatogram was obtained with an end capped $C_8$ 5 micron, 4.5×250 mm column. The mobile phase used was 52% HISB and 48% acetonitrile at 1.5 mL/min. The chromatogram's major peaks are expressed as retention time in minutes and (area percent): 3.46 min. (2.9%), 4.02 min., (78.6%), 4.44 min , (6.12%), 5.49 min. (2.12%), 7.18 min. (9.30%).

The proton NMR of this substance was recorded in methanol-$d_4$ with tetramethylsilane (TMS) as the internal standard. The chemical shifts of the major signals are reported in parts per million (ppm) downfield from TMS; 2.1 ppm, 3.8 ppm, 4.85 ppm, 6.3 ppm, 6.48 ppm, 6.75 ppm.

The carbon-13 NMR spectrum of this substance was recorded in methanol-$d_4$ with tetramethylsilane (TMS) as the internal standard. The chemical shifts of the major signals are reported downfield from TMS; 20.71 ppm, 31.09 ppm, 108.34 ppm, 120.83 ppm, 121.28 ppm, 129.49 ppm, 129.72 ppm, 130.43 ppm, 134.17 ppm, 144.12 ppm, 145.29 ppm, 149.90 ppm.

EXAMPLE 4

Novolak Oligomer D 2,6-Bis[2,4,6-trihydroxyphenyl)methyl]-4-methylphenol

A 3 L three necked flask was fitted with a mechanical stirring apparatus, a Y arm, and a thermometer. To the flask was added 2,6-bis(hydroxymethyl)-p-cresol (recrystallized once from ethanol) (25.26 g, 0.15 mole), phloroglucinol dihydrate (364.8 g, 2.25 moles), p-toluene sulfonic acid monohydrate (6.0 g) and water (2400 mL). Stirring was begun and the mixture was heated to 60 degrees C. and maintained at about 60 degrees C. for four hours. The reaction mixture was filtered at the end of the heating period and allowed to cool.

The solid was isolated by filtration and was extracted with warm (about 45 degrees C.) water (3×2200 mL). The solid material remaining after extraction was dried in vacuum to leave 13 g of solid.

The titled compound's purity and identity were established by its liquid chromatogram, proton NMR and carbon-13 NMR spectra.

This substance's liquid chromatogram was obtained using 5 micron 4.5 mm×250 mm endcapped $C_8$ column. The mobile phase was 52% HISB and 48% acetonitrile at 1.5 mL/min. The chromatogram exhibited the following major peaks reported as retention time in minutes and (area percent); 3.32 min. (86.13%), 4.43 min. (11.30%).

The proton NMR of this substance was recorded in methanol-$d_4$ with tetramethylsilane (TMS) as the internal standard. The major signals are reported in parts per million (ppm) downfield from the TMS; 2.12 ppm, 3.82 ppm, 4.85 ppm, 5.95 ppm, 6.95 ppm.

The carbon-13 NMR of this substance was recorded in methanol-$d_4$ with tetramethylsilane (TMS) as the internal standard. The major signals are reported in parts per million (ppm) downfield from the TMS; 20.86 ppm, 23.99 ppm, 95.83 ppm, 107.56 ppm, 128.88 ppm, 129.88 ppm, 130.16 ppm, 149.65 ppm, 157.22 ppm, 157.42 ppm.

EXAMPLE 5

Photoactive Compound M

Esterification of One Mole of Novolak Oligomer A with Three Moles of 6-Diazo-5,6-dihydro-5-oxo-napthalene-1-sulfonic Acid Chloride A One L beaker was wrapped with aluminum foil and fitted with a mechanical stirring apparatus and a pH probe. 2,6-Bis[(5-chloro-4,6-dihydroxyphenyl)methyl]-4-methylphenol oligomer (12.0 g, 0.0285 mole), 6-diazo-5,6-dihydro-5-oxo-naphthalene-1-sulfonic acid chloride (22.95 g, 0.0854 mole), tetrahydrofurfural alcohol (400 mL) and water (40 mL) were mixed into the beaker.

Triethylamine was added dropwise until the pH had stabilized at 7.4. After stirring for ten minutes, the reaction mixture was acidified to pH 1.25 with of 32% hydrochloric acid (1.2 g). This product was precipitated into water (2 L) which had been acidified with 32% hydrochloric acid (19 g).

The yellow product was isolated by filtration, washed with water (2 L), and dried under vacuum 24 hours to yield 31.3 of yellow product.

The number of components in the mixture was determined using liquid chromotography. A 5 micron 4.5 mm×250 mm endcapped $C_8$ column was used. The mobile phase was 45% HISB 55% acetonitrile at 2.5 mL/min. The major components of the chromatogram are reported as retention time in minutes and (area percent); 5.3 min. (2.6%), 6.9 min. (5.5%), 7.6 min. (3.54%), 11.2 min. (20.1%), 17.39 min. (9.7%), 23.9 min. (48.8%).

EXAMPLE 6

Photoactive Compound N

Esterification of One Mole of Novolak Oligomer A with Four Moles of 6-Diazo-5,6-dihydro-5-oxo-naphthalene-1-sulfonic Acid Chloride A one L beaker was wrapped with aluminum foil and fitted with a mechanical stirring apparatus and a pH probe. To the beaker was added 2,6-bis[(5-chloro-2,4-dihydroxyphenyl)methyl]-4-methylphenol oligomer(10.0 g 0.0234 mole), 6-diazo-5,6-dihydro-5-oxo1-naphthalene sulfonic acid chloride (24.98 g, 0.093 mole), tetrahydrofurfural alcohol (440 mL) and water (40 mL).

To the stirred reaction mixture was added triethylamine until the pH of the mixture was stable at 7.7. After stirring one hour the reaction mixture was quenched with 32% hydrochloric acid (1.8 g). The product was precipitated into water (2 L) which had been acidified with 32% hydrochloric acid (19 g).

The solid was isolated by filtration, washed with water (4 L), and dried under vacuum 24 hours to yield 32.1 g of yellow product.

The number of components in the mixture was determined by liquid chromatography. A 5 micron 4.5 mm×250 mm endcapped $C_8$ column was used. The mobile phase was 45% HISB, 55% acetonitrile at 2.5 mL/min. The major components of the chromatogram are reported as retention time in minutes and (area percent); 1.95 min (1.99%), 6.85 min. (3.97%), 17.31 min. (10.91%), 23.71 min. (43.76%), 23.56 min. (33.05%).

EXAMPLE 7

Photoactive Compound O

Esterification of One Mole of Novolak Oligomer B with Three Moles of 6-diazo-5,6-dihydro-5-oxo-naphthalene-1-sulfonic Acid Chloride A three neck round bottom flask was fitted with a mechanical stirring apparatus and a pH probe. To the flask was added 2,6-bis-[(2,4-dihydroxyphenyl)methyl]-4-methylphenol oligomer(7.0 g, 0.0199 mole), 6-diazo-5,6-dihydro-5-oxo-1-naphthalene-1-sulfonic acid chloride (16.0 g, 0.0597 mole), and gamma-butyrolactone (70 mL).

To the solution was added 4-dimethylaminopyridine (7.7 g) in acetone (80 mL) over about 30 minutes at a pH greater than 7. The mixture was allowed to stir one hour after the completion of addition.

The product was precipitated into water (1 L) which had been acidified to pH 3 with concentrated hydrochloric acid and stirred 30 minutes, isolated by filtration, and washed with water (2×500 mL). The solid was reslurried in water (500 mL) for 30 minutes, and was isolated again by filtration.

The solid was dried in vacuum at about 40 degrees C. for 24 hours. The Yield was 18.3 g.

The number of components in the mixture was determined by liquid chromatography. The column was a Waters Nova-Pac Type 8NVC184. The mobile phase was 62% buffer, 38% acetonitrile at 2 mL/min. The major components are reported as retention time in minutes and (area percent); 1.67 min. (2.92%), 2.92 min. (4.85%), 4.08 min. (7.98%), 5.92 min. (24.94%), 11.7 min. (6.07%), 13.61 min. (30.50%), 19.06 min. (4.0%), 22.75 min (2.03%).

EXAMPLE 8

Photoactive Compound P

Esterification of One Mole of the Novolak Oligomer C with Four Moles of 6-Diazo-5,6-dihydro-5-diazo-naphthalene-1-sulfonic Acid Chloride A three neck round bottom flask was fitted with a mechanical stirring apparatus and a pH probe. To the flask was added 2,6-bis[(2,3,4-trihydroxyphenyl)methyl]-4-methylphenol oligomer (7.00 g, 0.0182 mole), 6-diazo-5,6-dihydro-5-oxo-naphthalene-1-sulfonic acid chloride (19.6 g, 0.0729 mole), and gamma-butyrolactone (80 mL).

To the solution was added a solution of 4-dimethylaminopyridine (9.3 g) in acetone (100 mL) over 30 minutes, and the reaction was allowed to stir one hour after the end of addition.

The product was precipitated into distilled water (1 L) which had been adjusted to pH 1 with concentrated hydrochloric acid and stirred for 30 minutes. The solid was isolated by filtration, washed with water (2×500 mL), reslurried in distilled water (1 L) for 30 minutes and isolated again by filtration.

The solid was dried in vacuum at 40 degrees C. for 24 hours to yield 23.4 g of product.

The number or components of the mixture was determined by liquid chromatography. The column was a Waters Nova-Pac Type 8NVC184. The mobile phase was 62% buffer 38% acetonitrile at 2 mL/min. The buffer is made from water (1 L), phosphoric acid (1 mL), and triethylamine (1 mL). The major components are reported as retention time in minutes and (area percent); 1.47 min., (2.67%); 1.91 min., (4.95%); 2.25 min., (6.29%); 2.86 min., (2.64%); 3.36 min., (2.86%); 3.82 min., (24.73%); 4.64 min., (2.92%); 5.08 min., (12.39%); 6.33 min., (2.40%); 7.42 min., (2.48%); 9.92 min., (2,34%); 10.8 min., (21.33%); 13.68 min., (4.99%).

EXAMPLE 9

Photoactive Compound Q

Esterification of One Mole of Novolak Oligomer C with Six Moles of 6-Diazo-5,6-dihydro-5-oxo-naphthalene-1-sulfonic Acid Chloride A three neck round bottom flask was fitted with a mechanical stirring apparatus. To the flask was added 2,6-bis[(2,3,4-trihydroxyphenyl)methyl]-4-methylphenol oligomer (5.0 g, 0.0130 mole), 6-diazo-5,6-dihydro-5-oxo-naphthalene-1-sulfonic acid chloride (21.0 g, 0.0782 mole) and gamma-butyrolactone (80 mL).

To the stirred solution was added a solution of 4-dimethylaminopyridine (10 g) in acetone (100 mL) over 30 minutes. The reaction was allowed to stir one hour after the addition was complete.

The product was precipitated into water (1 L) which had been adjusted to pH 1 with concentrated hydrochloric acid and was stirred for 30 minutes. The solid and was isolated by filtration and washed with water (2 ×500 mL). The solid was reslurried for 30 minutes in water (1 L) and isolated again by filtration.

The solid was dried in vacuum at 40 degrees C. for 24 hours to obtain 21.0 g product.

The number of components in the mixture was determined by liquid chromatography. A Waters Nova-Pac Type NVC184 was used. The mobile phase was 62% buffer 38% acetonitrile at 2.0 mL/min. The major components are reported as retention in minutes and (area percent), 1.48 min. (3.02%), 10.77 min. (48.96%), 13.68 min. (35.72%), 28.67 min. (3.21%).

EXAMPLE 9A

Photoactive Compound R

Esterification of Novolak Oligomer C with Five and One Half Moles of 6-Diazo-5,6-dihydro-naphthalene-1-sulfonic Acid Chloride This photoactive compound mixture was formed by mixing one part by weight of the substance formed in example 8 with three parts by weight of the substance formed in example 9.

EXAMPLE 9B

Photoactive Compound S

Esterification of Novolak Oligomer C with Five Moles of 6-Diazo-5,6-dihydro-5-oxonaphthalene-1-sulfonic Acid Chloride This photoactive compound mixture is formed by mixing equal weights of the substances formed in example 8 with that formed in example 9.

EXAMPLE 10

Photoactive Compound T

Esterification of the Novolak Oligomer D with Four Moles of 6-Diazo-5,6-dihydro-5-oxo-naphthalene-1-sulfonic Acid Chloride A three neck round bottom flask was fitted with a mechanical stirring apparatus. To the flask was added 2,6-bis[(2,4,6-trihydroxyphenyl)methyl]-4-methylphenol oligomer (5.00 g, 0.0130 mole), 6-diazo-5,6-dihydro-5-oxo-naphthalene-1-sulfonic acid chloride (14.0 g, 0.521 mole), and gamma-butyrolactone (80 mL).

To the solution was added 4-dimethylaminopyridine (6.68 g) in acetone (100 mL) over 30 minutes. The reaction mixture was allowed to stir one hour after addition was completed.

The product was precipitated by pouring it into water (1 L) which had been acidified to pH 1 with concentrated hydrochloric acid and stirred 30 minutes. The solid was isolated by filtration and washed with water (2×500 mL). The solid was reslurried in water (500 mL) 30 minutes and isolated again by filtration.

The solid was dried at 40 degrees C. under vacuum for 24 hours to yield 15.9 g of product.

The number of components was determined by liquid chromatography. The column was a Waters Nova-Pak Type NVC184. The mobile phase was 62% buffer 38% acetonitrile at 2.0 mL/min. The major components are reported as retention time and (area percent). 1.46 min., (2.2%); 1.60 min., (2.7%); 1.88 min., (3.63%); 3.58 min., (10.7%); 7.46 min., (31.9%), 16.44 min., (31.77%).

EXAMPLE 11

Photoactive Compound U

Esterification of Novolak Oligomer D with Six Moles of 6-Diazo-5,6-dihydro-5-oxo-naphthalene-1-sulfonic Acid Chloride A three neck round bottom flask was fitted with a mechanical stirring apparatus. To the flask is added 2,6-bis[(2,4,6-trihydroxyphenyl)methyl]-4-methylphenol oligomer (5.22 g, 0.0135 mole), 6-diazo-5,6-dihydro-5-oxonaphthalene-1-sulfonic acid chloride (21.92 g, 0.0816 mole), and gamma-butyrolactone (80 mL).

To the solution was added 4-dimethylaminopyridine (10.44 g) in acetone (100 mL) over 30 minutes. The reaction mixture was allowed to stir one hour after addition was complete.

The product was poured into water (1 L) which had been acidified to pH 1 with concentrated hydrochloric acid and was stirred 30 minutes. The solid was isolated by filtration and washed with water (2 ×500 mL). The solid was reslurried in water (500 mL) for 30 minutes and isolated again by filtration.

The solid was dried under vacuum at 40 degrees C. for 24 hours to yield 21.9 g product.

The number of components was determined by liquid chromatography. The column was a Waters Nova-Pak NVC184. The mobile phase was 62% buffer and 38% acetonitrile. The major components are reported as retention time in minutes and (area percent); 1.48 min. (2.64%), 3.58 min. (2.41%), 16.3 min. (45.44%), 18.95 min. (42.96%).

EXAMPLE 12

NOVOLAK V

To a 5 L three neck round bottom flask equipped with a condenser, a mechanical stirrer, and a thermometer was added a m/p cresol mixture (m/p=45/55, 2004.6 g, 18.537 moles), formaldehyde (916 g, 37 weight percent solution, 11.3 moles). The solution was heated in an oil bath at 95° C. A solution of oxalic acid dihydrate (2.70 g) in hot water (20.0 g) was added. After 15 minutes, the oil bath temperature was raised to 110 degrees C. and maintained at this temperature for 15 hours.

The reaction temperature was then raised to 200° C. over two hours. During this time water and formaldehyde were removed by atmospheric distillation. The temperature was held at 200° C. for an additional two hours.

Then the reaction was subjected to a gradually increasing vacuum at 200° C. and maintained at 200 degrees C. for four hours to remove all substantially unreacted cresol monomers. The molten novolak was then poured onto a tray. The $M_w$ of the novolak was 7,200 by gel permeation chromatography.

EXAMPLE 13

NOVOLAK W

To a 5 L three neck flask equipped with a condenser, a mechanical stirring apparatus, and a thermometer, was added a m/p cresol mixture (m/p-40/60, 004.6 g, 18.537 moles) and formaldehyde (975.3 g, 37 weight percent, 12.05 moles). The mixture was heated to 95 degrees C. in an oil bath. To the solution was added oxalic acid dihydrate (2.70 g) in hot water (20.0 g). After 15 minutes, the oil bath temperature was raised to 110 degrees C. and maintained at this temperature for an additional 15 hours.

The reaction temperature was then raised to 200 degrees C. over two hours. During this time the water and formaldehyde were removed by atmospheric distillation. The temperature was held at 200 degrees C. for an additional two hours. The distillate weighed 890 g.

Then the reaction was subjected to gradually increasing vacuum at 200 degrees C. and maintained at 200 degrees C. for four hours to remove substantially all of unreacted cresol monomers. The molten novolak was poured onto a tray. The weight was about 1500 g.

The $M_w$ of the novolak was 6910 by gel permeation chromatography.

EXAMPLE 14

NOVOLAK X

A portion (42.9 g) of the novolak from example W was dissolved in 2-ethoxyethyl acetate (25.67 g) and methanol.(45.1 g) in a glass container. A solution of methanol (55.9 g) and water (72.8 g) was added to the solution. The container was sealed and the mixture was allowed to roll horizontally at ambient temperature for one hour and allowed to stand overnight. Upon standing, the mixture separated into two layers. The milky upper layer was substantially separated from the lower layer by decanting and siphoning.

The lower layer was distilled at about 200 degrees C. for one hour at atmospheric pressure, and then it was subjected to a gradually increasing vacuum and allowed to distill under high vacuum at 200 degrees C. for two hours and forty minutes. The molten novolak was isolated by pouring it onto aluminum foil. The product weighed 32.8 g.

EXAMPLE 15

NOVOLAK Y

To 1 L three neck round bottom flask, equipped with a condenser, a mechanical stirring apparatus, and a thermometer, was added m/p-cresol mixture (m/p 40/60, 421.1 g, 3.89 moles) and formalin (196.0 g, 37 weight percent, 2.42 moles). The reaction mixture was heated in an oil bath to 95° C. and a solution of oxalic acid dihydrate (2.70 g) in hot water (20.0 g) was added. After 15 minutes, the oil bath's temperature was raised to 110 degrees C. and maintained at this temperature for 15 hours.

The reaction temperature was then raised to 200 degrees C. over two hours. During this time water and formaldehyde were removed by atmospheric distillation. The temperature was held at 200 degrees C. for an additional two hours.

The temperature was raised to 230 degrees and the reaction mixture was subjected to a gradually increasing vacuum. It was held at 230 degrees C. for one hour. The temperature was then increased to 250 degrees C. and maintained at that temperature for 4.5 hours to remove substantially all unreacted cresol monomers. The molten novolak was poured onto a tray. The yield was 2.73.1 g.

The $M_w$ of the novolak was 7690 by gel permeation chromatography.

EXAMPLE 16

NOVOLAK Z

To a 5 L three neck round bottom flask equipped with a condenser, a mechanical stirring apparatus, and a thermometer was added a mixture of m/p-cresols (40/60 m/p-, 2004.6 g, 18.537 moles) aqueous formaldehyde and (992 g, 37 weight percent, 12.23 moles). The solution was heated in an oil bath at 95 degrees C. To the solution was added oxalic acid dihydrate (2.70 g) in hot water (20.0 g). After 15 minutes, the oil bath temperature was increased to 110 degrees C. and maintained at this temperature for 15 hours.

The reaction temperature was raised to 200 degrees C. over two hours. During this time the water and formaldehyde were removed by atmospheric distillation. The temperature was held at 200 degrees C. for an additional 2 hours.

The reaction was subjected to a gradually increasing vacuum at 200 degrees C. and maintained at 200 degrees C. for four hours to remove substantially all unreacted cresol monomers. The molten novolak was poured onto an aluminum foil tray. The yield was about 1500 g.

This novolak's MW by gel permeation chromatography was 7350.

EXAMPLES 17-43

Preparation of Photoresist Formulations

Photoresist formulations in Examples 17-43 were prepared by dissolving a photoactive compound of Example 5-11 and a novolak resin of Example 12-16 in ethyl lactate. The percent of photoactive compound in the total photoresist solids (i.e. sum of photoactive compound and novolak resin) is listed in Tables 1, 2 and 3 under the column S%.

The solids content of each photoresist was adjusted by dilution with more ethyl lactate to provide 1.2 micron films when spin coated somewhere in the range of 4000-6000 rpms.

The resist solutions were then filtered through a 0.2 micron pore-size filter.

Photoresist Processing

A. Coating of Photoresist Composition onto a Substrate

Photoresist solutions prepared above were spin-coated with a spinner onto a thermally grown silicon/silicon dioxide-coated wafers of 10 cm (four inches) in diameter and 5000 angstroms in oxide thickness which had been primed with hexamethyldisilazane (HMDS). Uniform coatings, after drying, of approximately 1.2 micron in thickness were obtained at spinning velocities ranging from 4,000 to 6,000 RPM for 30 seconds, depending upon the resist viscosity. The coated wafers were soft baked on a hot plate for 50 seconds at 110° C.

B. Exposure of Coated Substrates

A Nikon G line step and repeat exposure unit equipped with a 0.30 numerical aperture lens was used. This exposure tool provided a narrow spectral output at 436 nm.

C. Post Exposing Bake of Exposed Coated Substrates

The exposed photoresist coatings of Examples 35 and 37 and Comparison 3 were subjected to a post-exposure bake on a hot plate at 120° C. for one minute prior to development. The other exposed photoresist coatings were not subjected to this post exposure bake.

D. Development of Exposed Resist Coated Substrates

The exposed photoresist coatings of Examples 17-35 and 38-43 were puddle developed for 60 seconds using a 2.38% by weight tetramethyl ammonium hydroxide aqueous developer solution in a 2 second spray and 58 second dwell cycle followed by rinsing and spin drying. Examples 36 and 37 photoresist was developed in the same manner except that the developing solution contained 0.5% of a wetting agent, Pyonine-4050T made by Takemoto Oil & Fat Co. Ltd.

Comparisons 1-3

Comparison 1 photoresist formulation was made with a photoactive compound which was formed by the esterification of 1 mole of 2,3,4,4'-tetrahydroxy-benzophenone with 3 moles of 6-diazo-5,6-dihydro-5-oxo-napthalene-1-sulfonic acid chloride and the novolak resin of Example 5. The amount of the PAC was about 21% by weight as shown in Table 1. 2,3,4,4'-tetrahydroxy benzophenone is a commonly used chemical backbone for many commercial positive photoresist formulations.

Comparison 2 is a commercially available positive photoresist named 7950 available from Japan Synthetic Rubber Company.

Comparison 3 is the same photoresist 7950 which was processed with the post exposure bake step discussed above.

The photoresist formulation of Examples 17-43 and Comparisons 1-3 were evaluated for photospeed; line and space resolution; contact hole clearance, scum, profile and image deformation temperature.

Photospeed is the exposure energy required as measured in mJ/cm$^2$ to produce equal lines and spaces from corresponding equal lines and spaces on a mask. From the point of view of wafer throughput, it is desirable to have lower value for photospeed. An acceptable range for photospeed depends upon the application, but generally values below about 300mJ/cm$^2$ are very good.

Line and space resolution is the minimum line and space dimension as used in the tables measured in microns that can be resolved using the same exposure energy required to resolve one micron equal lines and spaces. The smaller this measured value, the better the resolution of the resist.

Contact holes are very small circular or square features measured in microns which are cleared at the same exposure energy used to measure resolution. The smaller this measured value, the better the performance of the resist in this regard.

Scum is small amounts of residual photoresist remaining in exposed developed areas on the substrate. Scum is undesirable because it can interfere with subsequent processing. The amount of scum on the photoresists evaluated in the Tables was rated on a scale of 0 to 4, wherein 0 represents no scum observed by scanning electron micrographs whereas 4 represents substantial degree of scum observed by the same means. Small amounts of scum may be removed by alternative processing techniques as shown in Examples 34-37 with improvement of some of the other lithographic properties.

Profile is the slope of the side wall of resist lines at the smallest resolution values (i.e. those given in Tables 1, 2 and 3).

The more vertical the slope, the better is the profile. In the Tables, the profiles were determined by scanning electron micrograph examination and given values of 0, 1, or 2 wherein 0 represents an observed good profile and 2 represents an observed fair profile.

Image Deformation Temperature (expressed in ° C.) is the temperature at which the top corner of a large resist dimension begins to round. The higher the image deformation temperature, the greater the thermal resistance of the resist and the more suitable it is for applications which subject the resist to elevated temperature processing.

TABLE ONE

Lithographic Evaluation of Esterified Chlororesorcinol and Resorcinol Novolak Oligomers

| Photoresist | PAC | Novolak | S % | Photospeed | Resolution | Contact hole | Scum | Profile | Image Deformation Temp. |
|---|---|---|---|---|---|---|---|---|---|
| 17 | M | V | 22 | 265 | 0.7-0.75 | 0.9 | 0 | 1 | N.M. |
| 18 | N | V | 22 | >400 | N.M | N.M. | N.M. | N.M. | N.M. |

TABLE ONE-continued
Lithographic Evaluation of Esterified Chlororesorcinol and Resorcinol Novolak Oligomers

| Photoresist | PAC | Novolak | S % | Photospeed | Resolution | Contact hole | Scum | Profile | Image Deformation Temp. |
|---|---|---|---|---|---|---|---|---|---|
| 19 | O | V | 24 | 196 | 0.75–0.8 | 0.9 | 0 | 2 | 115–120 |
| C- | 3S/4HBP | V | 21 | 152 | 0.75–0.8 | 1.0 | 0 | 2 | 120 |

N.M. = Not Measured

TABLE TWO
Lithographic Evaluation of Esterified Pyrogallol Novolak Oligomers

| PHOTORESIST | PAC | NOVOLAK | S % | Photospeed | Resolution | Contact Hole | SCUM | PROFILE | Image Deformation Temperature |
|---|---|---|---|---|---|---|---|---|---|
| 20 | P | V | 19 | 69.7 | 0.85 | 1.0 | 0 | 1 | N.M. |
| 21 | P | V | 21 | 75.08 | 0.80 | 1:0 | 0 | 1 | 130 |
| 22 | P | V | 23 | 101.9 | 0.80 | 1.0 | 0 | 1 | N.M. |
| 23 | Q | V | 19 | 268.1 | 0.65 | 0.85 | 3 | 0 | N.M. |
| 24 | Q | V | 21 | 305.6 | 0.65 | 0.85 | 3 | 0 | 125 |
| 25 | Q | V | 23 | 391.5 | 0.65 | 0.85 | 3 | 0 | N.M. |
| 26 | Q | W | 17 | 251.5 | 0.65 | 0.85 | 2 | 0 | 125 |
| 27 | R | V | 19 | 201.9 | 0.65 | 0.9 | 3 | 0 | 125 |
| 28 | R | V | 21 | 239.1 | 0.65 | 0.9 | 2 | 0 | 125 |
| 29 | S | V | 23 | 212.5 | 0.65 | 1.0 | 3 | 0 | 125 |
| 30 | S | X | 21 | 264.1 | 0.65 | 0.90 | 3 | 0 | 125 |
| 31 | S | X | 23 | 289.2 | 0.65 | 0.9 | 3 | 0 | 125 |
| 32 | S | Y | 21 | 289.2 | 0.65 | 0.9 | 2 | 0 | 125 |
| 33 | S | Y | 23 | 345.8 | 0.65 | 0.9 | 3 | 0 | 125 |
| 34 | S | Z | 21 | 355.1 | 0.70 | 0.90 | 3 | 0 | 125 |
| 35 | S | Z | 21 | 397.5 | 0.70 | 0.90 | 2 | 0 | 135 |
| 36 | S | Z | 21 | 296.8 | 0.75 | 0.90 | 1 | 0 | 125 |
| 37 | S | Z | 21 | 344.5 | 0.70 | 0.85 | 0 | 0 | 140 |

N.M. = Not Measured

TABLE THREE
Lithographic Evaluation of Esterified Phloroglucinol Novolak Oligomers

| PHOTORESIST | PAC | NOVOLAK | S % | PHOTOSPEED | RESOLUTION | Contact Hole | SCUM | PROFILE | HEAT RES. |
|---|---|---|---|---|---|---|---|---|---|
| 38 | T | V | 19 | 123.3 | 0.80 | 1.0 | 0 | 1 | N.M. |
| 39 | T | V | 21 | 134.1 | 0.80 | 1.0 | 0 | 1 | 125 |
| 40 | T | V | 23 | 187.7 | 0.75 | 1.0 | 0 | 1 | N.M. |
| 41 | U | V | 19 | 327.1 | 0.65 | 0.85 | 3 | 0 | N.M. |
| 42 | U | V | 21 | 396.8 | 0.65 | 0.90 | 3 | 0 | 125 |
| 43 | U | V | 23 | 445 | N.M. | N.M. | N.M. | N.M. | N.M. |
| C-2 | UN | UN | UN | 169.6 | 0.80 | 1.00 | 2 | 0 | 120 |
| C-3 | UN | UN | UN | 206.7 | 0.70 | 0.90 | 0 | 0 | 135 |

UN = Unknown
N.M. = Not Measured

What is claimed is:

1. A trinuclear novolak oligomer of the formula (I):

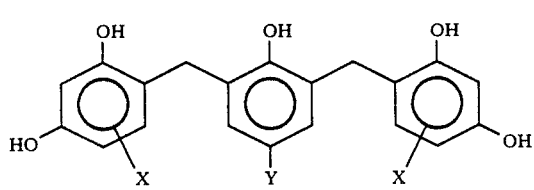

wherein each X is selected from the group consisting of hydrogen, hydroxyl group and halide group and Y is selected from the group consisting of a lower alkyl group having 1–4 carbon atoms and a halogen atom.

2. The trinuclear novolak oligomer of claim 1 wherein X is OH and Y is CH₃ or Cl.

3. The trinuclear novolak oligomer of claim 1 having the formula:

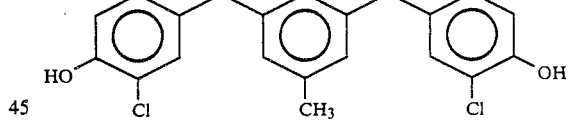

4. The trinuclear novolak oligomer of claim 1 having the formula:

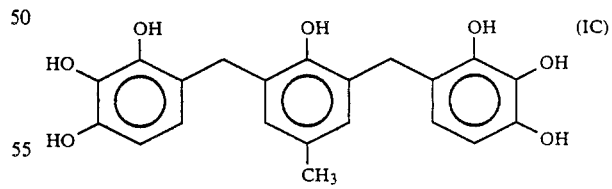

5. The trinuclear novolak oligomer of claim 1 having the formula:

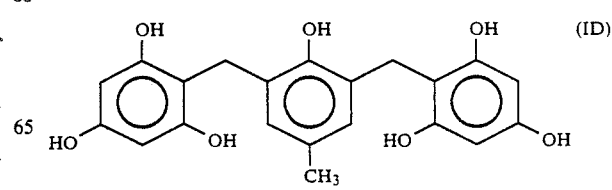

* * * * *